United States Patent [19]

Daddona et al.

[11] Patent Number: 5,026,537

[45] Date of Patent: Jun. 25, 1991

[54] METHODS FOR IMAGING ATHEROSCLEROTIC PLAQUE

[75] Inventors: Peter E. Daddona, West Chester; Harvey J. Berger, Devon, both of Pa.; Rodger P. McEver, Oklahoma City, Okla.

[73] Assignee: Centocor, Inc., Malvern, Pa.

[21] Appl. No.: 334,459

[22] Filed: Apr. 6, 1989

[51] Int. Cl.$^5$ .............................................. A61K 49/02
[52] U.S. Cl. .................................... 424/1.1; 424/85.91
[58] Field of Search .......................... 424/1.1, 9, 85.91

[56] References Cited

U.S. PATENT DOCUMENTS

| | | | |
|---|---|---|---|
| 3,875,299 | 4/1975 | Winchell et al. | 424/1.1 |
| 4,036,945 | 7/1977 | Haber . | |
| 4,359,453 | 11/1982 | Gordon | 424/1.1 |
| 4,577,636 | 3/1986 | Spears | 128/659 X |
| 4,610,241 | 9/1986 | Gordon | 424/9 X |
| 4,820,505 | 4/1989 | Ginsberg et al. | 424/9 |
| 4,877,599 | 10/1989 | Lees . | |

OTHER PUBLICATIONS

McEver et al., *J. Biol. Chem.* 258:5269–5275 (1983).
McEver and Martin, *J. Biol. Chem.* 259:9799–9804 (1984).
Stenberg et al., *J. Cell Biol.* 101:880–886 (1985).

*Primary Examiner*—John S. Maples
*Attorney, Agent, or Firm*—Hamilton, Brook, Smith & Reynolds

[57] ABSTRACT

This invention pertains to a method of imaging atherosclerotic plaque using radiolabeled monoclonal antibodies that are specific for activated platelets or activated endothelial cells. The method is capable of determining the site of endothelial injury. This method involves the administration of a platelet-specific labeled monoclonal antibody or antibody fragment to a patient. The antibody is allowed to accumulate at the plaque site and the plaque is then scanned with a photoscanner. The detected signals are then converted into an image of the plaque.

6 Claims, 1 Drawing Sheet

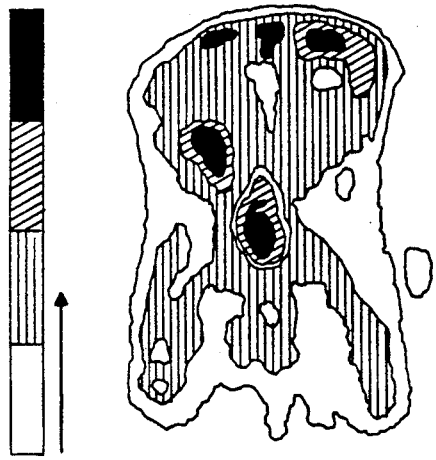
FIG. IA
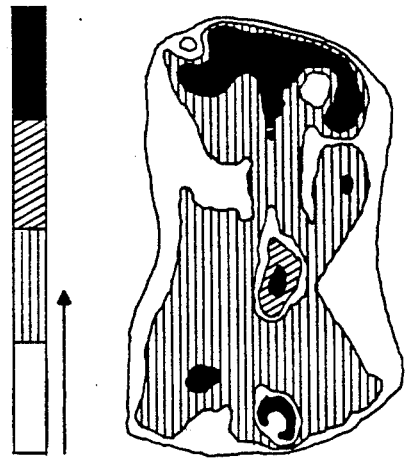
FIG. IB
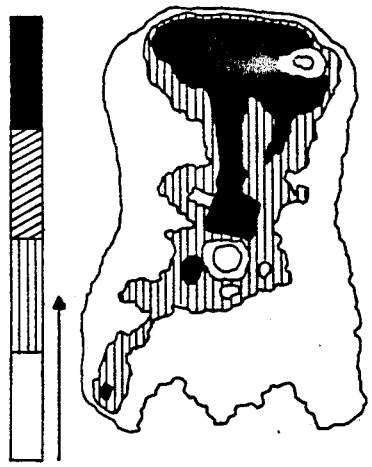
FIG. 2
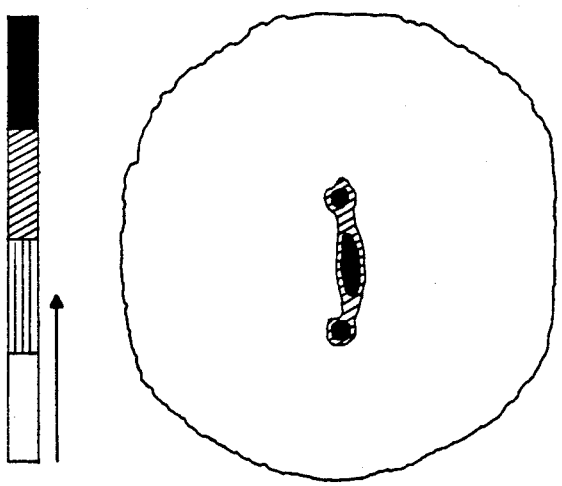
FIG. 3

METHODS FOR IMAGING ATHEROSCLEROTIC PLAQUE

DESCRIPTION

Background of the Invention

A generally accepted theory of development of atherosclerotic plaque is based on injury to the endothelial cells which line the inside surface of a blood vessel. The initial injury can be caused by chemical factors related to chronically elevated levels of cholesterol in the blood or by mechanical stress associated with hypertension.

The clinical effects of atherosclerotic plaque are due to its space occupying characteristics which lead to stenosis (narrowing) or its thrombogenic (clot-causing) characteristics which appear related to rupture of the fibrous cap and the resulting ulceration of the plaque surface. As a result, a thrombus will form at the site of the plaque. This, in turn, will almost invariably lead to acute myocardial infarction if present in coronary arteries. See Friedman et al., *Am. J. Pathol.*, 48:19–25 (1966); Schwartz, C.J. *Atherosclerosis*, 15:1–4 (1972).

It appears that the first stage of plaque formation is caused by macrophages migrating through the injured endothelium and accumulating subendothelially. The lesion is enlarged by an accumulation of smooth muscle cells which combine with the macrophages to form foam cells in fatty streaks. Endothelial cells appear to then separate, exposing much of the fatty streak to the circulation. This ulcerated condition provides opportunities for platelet aggregation and mural thrombosis. Damage to the endothelium and the resulting platelet activation may also cause further enlargement of the plaque.

The important consequence of these effects is reduction of blood flow to the affected organ (heart, brain, etc.). Atherosclerosis is the underlying cause of 75% of the one million deaths from cardiovascular disease in the United States each year. Atherosclerosis accounts for a large proportion of heart attacks, many strokes, most aneurisms of the lower abdominal aorta, and many cases of peripheral vascular disease. Myocardial infarcts have been imaged with antibodies that localize at the infarct site. See, e.g., Haber et al., U.S. Pat. No. 4,036,945. A need exists for imaging methods of high reliability and high resolution that can be used for diagnosing and monitoring atherosclerotic lesions. This is especially true for those lesions that have ulcerated or fissured, resulting in formation of blood clots.

SUMMARY OF THE INVENTION

This invention pertains to an method of imaging atherosclerotic plaques in vivo. The method entails the use of monoclonal antibodies specific for activated platelets or activated endothelial cells. According to the method of this invention, a radiolabeled monoclonal antibody or antibody fragment specific for activated platelets, such as the monoclonal antibody S12 which is specific for the GMP-140 glycoprotein of activated platelets or activated endothelial cells, is administered to a patient suspected of having an endothelial injury such as an ulcerated atherosclerotic lesion. The radiolabeled monoclonal antibody is allowed to accumulate at the site of the plaque. Thereafter, the signal generated by the radiolabel is detected by a photoscanning device and the signal is converted to an image of the atherosclerotic plaque.

BRIEF DESCRIPTION OF FIGURES

FIG. 1 shows schematic representations of planar imaging of technetium-99m (Tc-99m) S12 Fab' in rabbits. The increasing intensity of radiolabel uptake is shown by the direction of the arrow in the figure legend.

FIG. 1A shows a schematic diagram of Tc-99m S12 Fab' uptake and distribution in a control rabbit.

FIG. 1B shows a schematic diagram of Tc-99m S12 Fab' uptake and distribution in an atherosclerotic rabbit with repeat endothelial injury.

FIG. 2 shows a schematic diagram of Tc-99m S12 Fab' uptake and localization in the aorta of an atherosclerotic rabbit.

FIG. 3 shows a schematic representation of Tc-99m S12 Fab' uptake and distribution in the excised aorta of the same rabbit as shown in the previous Figure.

DETAILED DESCRIPTION OF THE INVENTION

An immunoscintigraphic image of an atherosclerotic plaque can be obtained with radiolabeled antibodies specific for activated platelets or activated endothelial cells. An antibody or antibody fragment (antigen binding fragment) specific for activated platelets or activated endothelial cells conjugated to a label which generates a signal detectable by external scintigraphy is administered to a patient suspected of having an atherosclerotic plaque. Sufficient time is allowed for the labeled antibody to localize at the site or sites of plaque. The signal generated by the label is detected by a photoscanning device and the signal is then converted to an image of the atherosclerotic plaque.

Preferred antibodies for plaque imaging are specific for an epitope of the GMP-140 protein, a marker of activated platelets. The protein is localized in alpha-granule membranes in unstimulated platelets. After thrombin stimulation and membrane fusion, the protein is redistributed to the cell surface and plasma membrane. The protein, GMP-140 has been described by Stenberg et al., *J. Cell Biol.*, 101, 880 1985.

In addition to being highly specific for activated platelets, antibodies specific for the GMP-140 glycoprotein have another advantage. The antibodies also react with endothelial GMP-140. Endothelial GMP-140, like its platelet counterpart, is localized to the membranes of secretory storage granules in unstimulated endothelial cells. When these cells are activated, the protein redistributes to the cell surface, just as it does in activated platelets. Thus, GMP-140 can serve a role as a marker of activated endothelial cells damaged by atherosclerotic ulceration or other endothelial injury. Imaging methods of this invention employing platelet-specific monoclonal antibodies are able to detect sites of endothelial injury in which vascular lesions are associated with platelet activation. These ulcerated or ruptured sites of plaque formation can be detected using platelet-specific monoclonal antibodies.

A particularly preferred antibody for the method of this invention is the monoclonal antibody S12 which reacts specifically with the GMP-140 protein. The S12 antibody reacts minimally with unstimulated human platelets but binds extensively after platelets have been activated with thrombin. See McEver and Martin, *J. Biol. Chem.*, 259:9799 (1984) incorporated herein by reference.

Antibodies against components of activated platelets other than GMP-140 may also be used. For example, the monoclonal antibody Tab, which binds to platelet glycoprotein IIb, can also be used in embodiments of this invention. See McEver et al., *J. Biol. Chem.*, 258:5269 (1983), incorporated herein by reference.

GMP-140 specific monoclonal antibodies of this invention are produced by hybrid cell lines commonly known as hybridomas. These hybrid cells are formed by fusion of an anti-GMP-140 antibody producing cell and an immortalizing partner (i.e. a cell line which imparts long term tissue culture stability to the hybrid cell). In the formation of the hybrid cell lines, the anti-GMP-140 antibody producing cell can be a B lymphocyte obtained from an animal or human who has developed an immune response to GMP-140: (i) naturally; (ii) as a result of a pathologic process; (iii) as a consequence of having been immunized with material containing GMP-140 such as activated platelets, activated endothelial cells, or a biological preparation comprising GMP-140. The immortalizing partner can be a cell of B lymphocyte lineage such as a B lymphoblastoid cell line or a plasmacytoma cell such as a myeloma cell, itself a antibody producing cell that is also malignant.

In particular, murine hybridomas producing GMP-140-specific monoclonal antibodies are formed by fusion of: (i) mouse myeloma cells and (ii) spleen cells from mice immunized against GMP-140 positive platelets or endothelial cells, purified GMP-140, or other biological preparations containing GMP-140. Fusions are accomplished by standard procedures well known in the art. Kohler and Milstein, *Nature*, 256, 495–497 (1975) and Kennet, *Monoclonal Antibodies* (Kennet et. al., eds.), pp. 365–367, Plenum Press. N.Y. 1980). The resulting murine hybridoma clonés are then screened for production of antibody reactive with GMP-140-positive platelets, endothelial cells, or preparations containing GMP-140. Those which secrete antibodies of the appropriate reactivity and specificity are cloned to yield a homogeneous cell line secreting anti-GMP-140 antibody.

Human hybridomas which produce monoclonal anti-GMP-140 antibodies are formed from the fusion of: (i) human B cells from an individual producing anti-GMP-140 antibodies and (ii) human B lymphoblastoid or human/human.mouse myeloma cells. The fusion partner for the myeloma cell may be an anti-GMP-140-producing B lymphocyte derived from the blood, spleen, or tonsil lymph node. The fusion and screening techniques are essentially the same as those used in the production and screening of murine anti-GMP-140 generating hybridomas.

Mouse/human hybridomas which produce human anti-GMP-140 antibody can be formed from the fusion of human antibody-producing cells and a murine plasmacytoma cell or a cell which itself is a hybrid having the appropriate properties such as the ability to fuse with human lymphocytes at a high frequency; support the synthesis and secretion of high levels of antibody; and support secretion of antibody for prolonged periods of time in culture.

Another way of forming the anti-GMP-140-producing cell line is by transformation of antibody-producing cells. For example, an anti-GMP-140 producing B lymphocyte may be infected and transformed with a virus such as Epstein-Barr virus to yield an immortal anti-GMP-140 producing cell. Kozbor and Roder, *Immunology Today*, 4, 72–79 (1983). Alternatively, the B lymphocyte may be transformed by a transforming gene or gene product.

GMP-140 specific monoclonal antibodies are produced in large quantities by injecting anti-GMP-140 antibody producing hybridomas into the peritoneal cavity of mice or other appropriate hosts and, after appropriate time, harvesting the resulting ascitic fluid which contains a high titer of antibody, and isolating the desired anti-GMP-140 monoclonal antibody therefrom. Allogeneic or xenogeneic hybridomas can be injected into immunosuppressed, irradiated or athymic nude mice. Alternatively, the antibodies may be produced by culturing anti-GMP-140 producing cells in vitro and isolating secreted monoclonal anti-GMP-140 antibodies from the cell cuture medium.

Antibody fragments, rather than whole antibody molecules, are generally preferred for use in the plaque-imaging method of this invention. Because they are distributed more readily in the tissues than are entire antibody molecules, antibody fragments accumulate at the target site more rapidly. Thus an image can be obtained in less time than is possible using whole antibody. These fragments are also cleared more rapidly from the circulation, resulting in a lower background signal. Haber et al., U.S. Pat. No. 4,036,945; Goldenberg et al., U.S. Pat. No. 4,331,647. The antigen binding fragments $F_v$, Fab, Fab' and $F(ab')_2$ or analogs of these fragments can be used. The Fab fragment can be prepared by digestion of whole immunoglobulin molecules with the enzyme papain; the $F(ab')_2$ fragment can be prepared by digestion of the whole immunoglobulin molecule with pepsin; and the Fab' fragment produced from the $F(ab')_2$ fragment by reduction with dithiothreitol or cysteine, according to any of several well known protocols. In addition, fragments can also be prepared by recombinant DNA techniques. See, for example, U.S. Pat. Application Ser. No. 195,720 (Coller and Knight), filed May 18, 1988, the teachings of which are incorporated by reference herein.

The antibodies or antibody fragments can be labeled with radioisotopes such as Indium-111 and Technetium-99m which are suitable for detection by external scintigraphy. The gamma-emitters Indium-111 and Technetium-99m are preferred because these radiometals are detectable with a gamma camera and have favorable half-lives in vivo. Technetium-99m is an ideal radionuclide for scintigraphic imaging because of its nuclear properties. It has a single photon energy of 140 KeV, a half-life of about 6 hours, and it is readily available from a $^{99}Mo$-$^{99m}Tc$ generator.

Antibodies can be labeled by any of the many techniques known in the art. The preferred technique for technetium-99m labelling is that of Pak, K.Y et al., U.S. Pat. Application Ser. No. 034,003, filed Apr. 2, 1987, the teachings of which are incorporated herein. Antibody can also be labeled with a radiometal via a chelating agent such as diethylene triaminepentaacetic acid (DTPA) which is conjugated to the antibody. In this indirect labeling approach, the radiometal is chelated by the chelating agent attached to the antibody See, for example, Khaw *et al.*, *Science*, 209:295–297 (1980) Krejcarek and Tucker, Biochem. Biophys. Res. Commun., 77:581–585 (1977); Childs and Hnatowich, *J. Nucl. Med.*, 26:293 (1985).

Various subtraction techniques can be used to enhance detection and/or localization of labeled antibodies. See, for example, Ballou, B. *et al., Science*, 206:844–847 (1979), and references cited therein.

The labeled antibody is administered to a patient in the form of an injectable composition. Injection may be intravenous or intraarterial. A typical composition contains a quantity of radiolabeled antibody sufficient for imaging (e.g., specific activity 3-150 mCi/mg) in neutral phosphate buffer containing physiological saline.

Photoscanning can be performed by standard techniques. Goldenberg et al., New Engl. J. Med., 298:1389 (1978) and references cited therein.

The method of this invention can be used to distinguish between ulcerated and nonulcerated atherosclerotic plaque. The method is clinically useful for monitoring the extent of progression of atherosclerosis in heart attack survivors and in screening a population at risk for atherosclerosis (about 143 million worldwide). Information provided by the methods of this invention will aid physicians in evaluation of therapy and in early diagnosis of atherosclerotic plaque.

This invention will now be more fully disclosed according to the following examples.

EXAMPLE I

Preparation of Technetium 99m-labeled anti-platelet Fab' fragment

A. Preparation of S12 Fab'

S12 IgG is purified from hybridoma tissue culture supernatant using Protein A Sepharose column chromatography. The F(ab')2 fragment is prepared from the IgG by pepsin proteolytic digestion at pH 3.9 and subsequently purified by cation exchange chromatography using for example, Pharmacia Fast Flow S. The Fab' fragment is produced from the F(ab')2 by reduction with dithiothreitol, purified by diafiltration or column gel filtration and formulated at 1-2 mg/ml in 50mM sodium phosphate buffer pH 6.3 containing 100mM sodium chloride and 1mM EDTA.

B. Labeling of S12 Fab' With Tc-99m

The S12 Fab' antibody fragment is labeled with Technetium 99-m as described by Pak et al., *Circulation* 76Supplement II, #2013 (1987); Pak et al U.S. Pat. Application Ser. No. 034,003 (filed Apr. 2, 1987). Using D.glucarate as the transfer ligand, 200-400 μg aliquots of the Fab' are labeled with Tc-99m to a specific activity of 10-40 mCi/mg. Final protein concentrations are 0.5-1 mg/ml in the labeling solution. The quantitative incorporation of Tc-99m is determined by gel filtration HPLC equipped with a radiometric detector, ITLC and paper chromatography.

Immunoactivity of Tc-99m S12 Fab' is evaluated using a platelet binding assay with thrombin-activated or unactivated platelets.

In this method, platelets are isolated by differential centrifugation from ACD treated whole human blood taken from normal volunteers. In the assay a fixed number of washed platelets ($5 \times 10^7$/ml) in PBS with 1% bovine serum albumin (BSA) is incubated with varying concentrations of Tc-99m S12 Fab' or Tc-99m labeled control antibody in PBS with BSA, 1 mM EDTA (final conc.) to prevent platelet aggregation and 8 units/ml of bovine thrombin (final conc.). Thrombin is omitted from the assay when binding to resting platelets is evaluated. Incubations are performed at room temperature for 60-120 min. Platelets are washed by centrifugation and radioactivity bound to platelets determined using a gamma counter set for Tc-99m.

Specific saturable binding of Tc 99m S12 Fab' has been demonstrated using this assay. The specificity of binding is such that 200 ug/mL of unlabeled S12 IgG prevents the binding of Tc-99m S12 Fab' to attached platelets. The binding is also activation dependent since there is only a background level of binding in this assay using platelets which have not been exposed to thrombin. The labeled S12 Fab' reacts strongly with activated platelets isolated from human, baboon, and rabbit. The antibody shows weak to no reactivity with unactivated platelets from these same species.

EXAMPLE II

Imaging using Tc-99m S12 Fab' monoclonal antibody

A. Preparation of a Rabbit Atherosclrosis Model

Rabbits weighing 5-10 lbs. received a 2% cholesterol atherogenic diet in order to elevate serum cholesterol levels. The diet consisted of rabbit chow supplemented by cholesterol-enriched peanut oil to produce hypercholesterolemia (cholesterol - 500-1000 mg %). This control group was kept on the diet for 1-2 weeks. A more severe atheroslcerotic condition was induced in the test group using the Baumgartner technique. Baumgartner H.R., *Ges. Exp. Med.* 137, 227, (1963). In brief, the endothelial lining of the infra.renal aorta is stripped or denuded by percutaneous placement of a 4 French Fogarty catheter via a femoral arteriotomy under sterile conditions. The catheter is retrogradely advanced through the iliac artery under fluoroscopic guidance. The balloon tip is inflated with saline and then drawn three times from the level of the renal to the proximal right iliac artery. After endothelial injury, the high cholesterol atherogenic diet is continued for an additional 4-6 weeks until the arterial re-injury phase of the study. This model has previously been shown to cause significant atherosclerosis characterized by intimal thickening, foam cell lesions and neovascularization in 66% of the animals. Baumgartner H.R., *Ges. Exp. Med.* 137,227 (1963).

B. Tc-99m Fab' Imaging of Arterial Injury in Rabbit Atherosclerosis Model

All rabbits were modeled to have atherosclerosis of the lower aorta and proximal iliac artery using a Fogarty catheter injury followed by high cholesterol diet for 4-6 weeks, as described previously. Rabbits were divided into three groups of increasingly severe aortic injury as follows:

I. Control group (resting plaque);
II. Reinjury group (repeated balloon injury causing focal ruptured plaque and endothelial damage); and
III. Percutaneous transluminal angioplasty (PTA) with intravascular stent placement (repeated balloon injury and placement of a 1cm long wire mesh stent).

At the time of each imaging study, contrast angiography was performed to confirm the site of injury. Animals were not anticoagulated or pre-treated with anti-platelet medications.

Within 15 minutes of injury, each rabbit was injected with 5 mCi/400 μg of Tc-99m S12 Fab' via an ear vein. Serial 5 minute images were obtained for 60 minutes after injection using a Searle 37×gamma camera and high resolution collimator and analyzed on a MDS A2 computer. In vivo Tc-99m S12 Fab' uptake was quantitated 45-60 minutes post injection from planar image regions-of-interest to derive an injured to normal (I:N) aortic activity ratio. Results from the three subgroups of increasingly severe injury are shown in Table 1.

TABLE 1

| Group | Rabbits | Injury | S12 I:N Ratio |
|---|---|---|---|
| I. | 4 | Control | 1.2 ± 0.17 |
| II. | 6 | Reinjury | 1.5 ± 0.18 |
| III. | 3 | PTA/Stent | 1.9 ± 0.12 |

The reinjury (II) and PTA/Stent (III) groups showed distinct focal Tc-99m S12 Fab' uptake that was significantly greater than that of control group I ($p<0.01$). Ex vivo imaging of the blood-free excised aortas confirmed marked S12 localization with an I:N $-3.2 \pm 1.4$ at pathologically and angiographically proven injury sites.

These results demonstrate that Tc-99m S12 Fab' localizes sites of active platelet degranulation in balloon-injured atherosclerotic endothelium with high specificity. Further, the degree of S12 uptake is proportional to the severity of the arterial injury.

Intense and focal uptake of Tc-99m S12 Fab' was demonstrated in the reinjury and PTA stented atherosclerotic model relative to the control atherosclerotic rabbits using planar imaging. FIG. 1 shows a schematic diagram of the planar imaging of Tc-99m S12 Fab' in a representative control rabbit (FIG. 1A) and an atherosclerotic rabbit with repeat Fogarty injury (FIG. 1B). The control rabbit was imaged 35 min. after Tc-99m S12 Fab' injection and shows non.specific radiochemical uptake in the two kidneys (upper quadrant), the spleen (left mid.section) and the bladder (lower center). Minimal uptake is visible in the descended infra renal aorta (mid.line area). An atherosclerotic rabbit with Fogarty treatment (FIG. 1B) shows intense radiochemical uptake in the upper infra renal aorta between the two kidneys (upper quadrant). Angiographic analysis of these rabbits (not presented here) clearly reveal the bulging aorta of the atherosclerotic rabbit relative to the control.

A complete set of in vovo and ex vivo images, angiograms, x-rays and pathology pictures was taken from a rabbit that received a PTA stent following atherosclerotic modeling and previous Fogarty balloon injury. FIG. 2 shows a schematic diagram of the radiolocalization of the Tc-99m S12 Fab' in the descending aorta of this rabbit taken 35 minutes after injection. Localization is noted as the intense streak in the area of the descending aorta. Sixty minutes after imaging, the rabbit was sacrificed, the descending aorta was excised, washed free of blood and mounted for pathological examination. Visual analysis revealed a mixture of white and red thrombus in the wire mesh of the stent and extensive atherosclerosis over the entire region of the aorta. A representation of the ex vivo image of the excised aorta indicating the localization of the Tc-99m S12 Fab' is shown in FIG. 3. These data, taken together show an excellent correlation of the atherosclerotic injury site by angiography, pathology and in vivo and ex vivo imaging using the Tc-99m S12 Fab' antibody.

Equivalents

Those skilled in the art will recognize or be able to ascertain, using no more than routine experimentation, many equivalents to the specific embodiments of the invention described herein. Such equivalents are intended to be encompassed in the following claims.

We claim:

1. A method of imaging an atherosclerotic plaque, comprising the steps of:
   a. administering to an individual suspected of having an atherosclerotic plaque, an effective amount of a radiolabeled monoclonal antibody or fragment thereof, specific for activated platelet or endothelial cell membrane protein GMP-140;
   b. allowing the radiolabeled monoclonal antibody or antibody-fragment to accumulate at the plaque site;
   c. detecting the signal generated by the radiolabel by means of a photoscanning device;
   d. converting the detected signal into an image of the plaque.

2. A method of claim 1, wherein the monoclonal antibody fragment is selected from the group consisting of Fab, Fab', F(ab')$_2$, and F$_v$ fragments.

3. A method of claim 1, wherein the monoclonal antibody is labeled with a radioactive material selected from the group consisting of Technetium-99m and Indium-111.

4. A method of claim 1, wherein the monoclonal antibody is S12.

5. A method of claim 1, wherein the atherosclerotic plaque is ulcerated or ruptured.

6. A method of imaging an atherosclerotic plaque. comprising the steps of:
   administering to an individual suspected of having atherosclerotic plaque, an effective amount of a $^{99m}$Tc-labeled Fab fragment of monoclonal antibody S12;
   b. allowing the radiolabeled antibody fragment to accumulate at the plaque site;
   c. detecting the signal generated by means of a gamma camera;
   d. converting the detected signal into an image of the plaque.

* * * * *